(12) United States Patent
Suijver

(10) Patent No.: US 8,428,695 B2
(45) Date of Patent: Apr. 23, 2013

(54) DIAGNOSTIC SYSTEMS AND METHODS UTILIZING PROBE-IONS EXHIBITING PHOTON AVALANCHE EFFECT

(75) Inventor: Jan Frederik Suijver, Dommelen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1241 days.

(21) Appl. No.: 12/294,961

(22) PCT Filed: Mar. 19, 2007

(86) PCT No.: PCT/IB2007/050949
§ 371 (c)(1),
(2), (4) Date: Sep. 29, 2008

(87) PCT Pub. No.: WO2007/110804
PCT Pub. Date: Oct. 4, 2007

(65) Prior Publication Data
US 2010/0234738 A1    Sep. 16, 2010

Related U.S. Application Data

(60) Provisional application No. 60/787,120, filed on Mar. 29, 2006.

(51) Int. Cl.
*A61B 6/00* (2006.01)
*A61B 5/0476* (2006.01)

(52) U.S. Cl.
USPC .......... 600/476; 600/554; 435/7.21; 435/7.92

(58) Field of Classification Search ............. 435/7.1, 435/7.21, 7.92; 436/73, 82, 86, 124, 127, 436/133, 154, 166, 172, 518; 600/476, 554
See application file for complete search history.

(56) References Cited

U.S. PATENT DOCUMENTS 5,891,656 A * 4/1999 Zarling et al. ............... 435/7.92
2005/0014283 A1    1/2005 Matsuura
2006/0140240 A1    6/2006 Chen

OTHER PUBLICATIONS

Marie-France Joubert, Photon avalanche upconversion in rare earth laser materials, Optical Materials 1999, 11, 181-203.*
Pascal Gerner et al., New Light Emission Processes in Inorganic Materials, Chimia, 2001, 55, 1021-1024.*
Guy, S. et al "Blue Avalanche Upconversion in TM:ZBLAN Fiber" J. Opt. Soc. Am. B, vol. 14, No. 4, Apr. 1997, pp. 926-934.
Bell, M.J.V. et al "Photon Avalanche Upconversion in TM 3+ Doped Fluoroindogallate Glasses" J. Phys. Condens, Mater vol. 14, pp. 5651-5663, 2002.
Chivian, Jay S. et al "The Photon Avalanche: a New Phoenomenon in Pr3+ based Infrared Quantum Counters" Applied Physics Letter. vol. 35, No. 2 Jul. 1979, pp. 124-125.
Gerner, Pascal et al "New Light Emission Processes in Inorganic Materials" Department of Chemistry and Biochemistry of the University Bern. vol. 55, 2001, pp. 1021-1024.
Shu, Q. et al "Nonlinear Dispersion of Avalanche Upconversion", Opticals Letters, vol. 22, No. 2, Jan. 15, 1997, pp. 123-125.
Yi, Guang-Shun et al "Rare-Earth Doped LaF3 Nanocrystals for Upconversion Fluorescence", National University of Singapore, Oct. 28, 2005.

* cited by examiner

*Primary Examiner* — Michael G Hartley
*Assistant Examiner* — Jagadishwar Samala

(57) ABSTRACT

The present disclosure provides advantageous systems and methods for significantly increasing the sensitivity and selectivity for diagnostic procedures, e.g., optical biopsy. The disclosed systems and methods use a highly non-linear effect, the so-called photon avalanche. In the regime close to the avalanche threshold, small differences in density of the probe-ion under investigation or the excitation power can result in very large changes in up-conversion emission intensity. Through this effect, it becomes possible to accurately measure the signal of an optical biopsy probe-ion only in the location(s) where its concentration is highest, while at the same time significantly reducing or eliminating measurement of background signal from probe-ions distributed with a somewhat lower concentration throughout the measurement volume. Also background auto-fluorescence of the surrounding healthy tissue is essentially absent with this technique.

19 Claims, 3 Drawing Sheets

DIAGNOSTIC SYSTEMS AND METHODS UTILIZING PROBE-IONS EXHIBITING PHOTON AVALANCHE EFFECT

This present disclosure is directed to systems and methods that exhibit increased sensitivity and/or selectivity in performing diagnostic procedures, e.g., optical biopsy. More particularly, the disclosed systems and methods employ probe-ions that exhibit a highly non-linear response to optical activation, i.e., a "photon avalanche" effect. The disclosed systems and methods exhibit increased sensitivity and/or selectivity because in the regime close to the avalanche threshold for a selected probe-ion, small differences in probe-ion density and/or excitation power translate to a substantial differential in up-conversion emission intensity. Through the use of the disclosed probe-ions, the systems and methods of the present disclosure accurately distinguish locations where the probe-ion concentration is high, e.g., above a desired threshold, while at the same time substantially eliminating background signals from probe-ions distributed at lower concentration throughout the measurement volume. In addition, background auto-fluorescence of surrounding healthy tissue is generally eliminated. Exemplary probe-ions for use according to the disclosed systems and methods include mixed rare earth/transition metal phosphors.

In the fields of medicine and biology, fluorescent materials are frequently used as markers. Fluorescence generated by irradiation of such materials with an appropriate activation energy is measured by an optical microscope, photo detector or the like. For example, antigen-antibody fluorescent methods are known in which an antibody is bound to an organic fluorescent body capable of emitting fluorescence. As the antigen-antibody reaction is highly selective, it is possible to identify the location of the antigen based on the distribution of fluorescence intensity. Selective binding and/or localization of fluorescent materials has wide-ranging applicability, e.g., in gene diagnosis, immunodiagnosis, medicinal development, environmental testing, biotechnology, fluorescent inspection, and the like.

An exemplary application of the foregoing luminescent-based technology is in the field of optical biopsy. In an optical biopsy, clinical and/or diagnostic information may be efficiently obtained in a non-invasive and/or minimally invasive manner. Thus, typical optical biopsy techniques are advantageous in that no tissue is destroyed and, depending on the marker(s) and other biopsy parameters, clinical and/or diagnostic information may be gathered over a relatively large surface area. Generally, optical biopsies involve the introduction of probe-ions to a patient and/or anatomical region of interest. The probe-ions generally include functionalised end-groups that are selected to preferentially bind to locations/tissues of interest, e.g., cancerous tissue. Thereafter, through optical or other energy-activation techniques, the luminescence of the probe-ions is recorded and a map may be constructed pinpointing the location of the markers within the patient and/or relative to anatomical structures of interest.

Several problems exist with respect to conventional optical biopsy systems and techniques. First, as a practical matter, not all the probe-ions are transferred to and/or centralized in the desired marker location. Oftentimes, a substantial fraction of the ions will not end up at the desired marker location and, due to their dispersion, will negatively effect the quality and/or accuracy of the biopsy results, e.g., by effecting the background signal so as to make it difficult to separate out or isolate the desired signal. Second, excitation in the visible region of the spectrum is usually required. At wavelengths in the visible region, many constituents of human tissue tend to auto-fluoresce. The auto-fluorescence of other tissue-types is an undesirable effect, increasing the difficulty associated with resolving and/or isolating luminescence from probe-ions at a specific marker location.

Materials and techniques for energy-activated fluorescence have been disclosed in the literature. For example, semiconductor nanocrystals (e.g., quantum dots (QDs)) have been disclosed for use as bio-probes for analytical and biophysical applications. Both QDs and fluorescent organic dyes are down-conversion fluorescent bio-probes, which emit lower energy fluorescent photon(s) after absorbing higher energy UV or visible photon(s). In addition, up-conversion fluorescent nanocrystals have been chemically synthesized from Yb—Er, Yb—Ho and Yb—Tm co-doped with $LaF_3$. Such nanocrystals have been used to produce green, red and blue emission bands based on 980 nm near-infrared (NIR) excitation. See, Guang-Shun Yi and Gan-Moog Chow, "Rare-earth doped $LaF_3$ nanocrystals for upconversion fluorescence," National University of Singapore. Similarly, U.S. Patent Publication No. 2005/0014283 to Matsuura et al. discloses a fluorescent probe that includes fine particles containing a rare earth element that is excited for up-conversion by light in the 500 to 2000 nm range. The Matsuura '283 publication contemplates use of a rare earth metal (e.g., Er, Ho, Pr, Tm, Nd, Gd, Eu, Yb, Sm or Ce) that is adapted to bind with a binding substance.

The prior art has also recognized and investigated the non-linear response associated with the "avalanche effect." For example, Q. Shu et al. have investigated two-beam coupling measurements of an avalanche up-conversion transition in concentrated $Tm:LiYF_4$, confirming that despite the resonate nature of the excited-state optical interaction, the induced response is strongly dispersive. See, Q. Shu, H. Ni and S.C. Rand, "Nonlinear dispersion of avalanche upconversion," Optics Letters, Vol. 22, No. 2, pages 123-125, Jan. 15, 1997. The test results reported in the foregoing publication show that the avalanche nonlinearity observed in $Tm:LiYF_4$ at 648.2 nm gives rise to beam coupling with a sharp threshold and a dispersive character at room temperature. Conventional up-conversion mechanisms have also been described in the literature, e.g., Pascal Gerner et al., "Chem. Eur. J.," 10, 4735-4741, 2004.

In terms of phosphor materials, research has been conducted with respect to $Tm^{3+}$ containing crystals and glasses, and on $Pr^{3+}$ doped glasses and fibers exist. See, e.g., S. Guy et al., "J. Opt. Soc. Am. B," 14(4), pp. 926-34, 1997; M J V Bell et al., "J. Phys.: Condens. Matter," 14, pp. 5651-5663, 2002; and J. Chivian et al., "Appl. Phys. Lett.," 35, 124 (1979). There are two important problems with prior art phosphor systems. First, the up-conversion avalanche emissions for such phosphors lie in the blue spectral range. At these wavelengths, many constituents of human tissue tend to absorb and auto-fluoresce. As a result, part of the emission light is lost and the signal is obscured. Second, the avalanche up-conversion process is relatively inefficient for these phosphors, requiring relatively high excitation densities which increase the risk of tissue damage due to laser ablation.

Thus, despite efforts to date, a need remains for systems and methods that exhibit increased sensitivity and/or selectivity in performing diagnostic procedures, e.g., optical biopsy. In addition, a need remains for systems and methods that accurately distinguish locations where probe-ion concentrations are high, e.g., above a desired threshold, while at the same time substantially eliminating background signals from probe-ions distributed at lower concentrations throughout the measurement volume. Further, a need remains for systems and methods that reduce and/or eliminate background auto-fluorescence of surrounding healthy tissue in performing diagnostic procedures, e.g., optical biopsy. These and other needs are satisfied by the systems and methods disclosed herein.

Systems and methods exhibiting increased sensitivity and/or selectivity in performing diagnostic procedures, e.g., optical biopsy, are disclosed herein. The disclosed systems and methods employ probe-ions that exhibit a highly non-linear response to optical activation, i.e., a photon avalanche effect, thereby permitting the generation of diagnostic readings/measurements with unparalleled signal-to-noise ratios. In the regime close to the avalanche threshold for a selected probe-ion, small differences in probe-ion density and/or excitation power translate to a substantial change in up-conversion emission intensity, thereby reliably, accurately and effectively distinguishing locations where the probe-ion concentration is high, e.g., above a desired threshold, while at the same time substantially eliminating background signals from probe-ions distributed at lower concentration throughout the measurement volume. The disclosed systems and methods also advantageously reduce and/or eliminate background auto-fluorescence of surrounding healthy tissue. Exemplary probe-ions for use according to the disclosed systems and methods include mixed rare earth/transition metal phosphors.

In exemplary embodiments of the present disclosure, probe-ions capable of an up-conversion avalanche effect are employed to improve the effectiveness of diagnostic procedures, e.g., optical biopsy. In selecting appropriate materials/compositions for use as probe-ions according to the present disclosure, materials/compositions are selected that are capable of up-conversion as well as exhibiting an avalanche effect at appropriate activation energy levels. In exemplary embodiments of the present disclosure, a rare earth ion in its trivalent state is employed as the probe-ion.

According to the present disclosure, probe-ions are introduced to the environment of interest, e.g., an anatomical environment. The probe-ions may be introduced in a variety of ways, as are known in the art, e.g., though injection, ingestion or the like. Based on binding affinities associated with the selected probe-ions, a higher concentration of the probe-ions is generally achieved in desired anatomical location(s). Generally, the probe-ions are allowed an appropriate period of time to preferentially/differentially concentrate in anatomical region(s) of interest, at which point probe-ion excitation is undertaken to facilitate a mapping/measurement of probe-ion concentration in the anatomical environment. The probe-ions are generally excited in the near-infrared region of the spectrum when taking an optical biopsy spectrum. At this excitation wavelength, i.e., an NIR wavelength, essentially no visible emission is generated by human tissue, thereby substantially overcoming and/or eliminating the issue of tissue auto-fluorescence associated with conventional probe-ion systems/techniques.

By choosing a probe-ion that exhibits the avalanche effect, the systems and methods of the present disclosure are able to translate relatively small variations/differentials in probe-ion density to relatively large variations/differentials in up-conversion emission. Therefore, based on the probe-ion selection, a suitable choice of excitation power can be made so as to initiate the avalanche effect for such probe-ion. The excitation power/energy is generally selected to be at or near the threshold value to initiate the avalanche effect for the probe-ions which have selectively congregated at the desired marker location(s), while the same power/energy is advantageously below the threshold value of initiating emissions for the lower concentration probe-ions located at distinct locations relative to the desired marker location(s), thereby avoiding/minimizing the potential for disruptive generation of background signals.

The up-conversion emission intensity advantageously scales almost exponentially with probe-ion concentration in the power-regime at or close to the avalanche threshold. Initiation of the avalanche effect thus results in strong luminescence from probe-ions in the desired marker location, and a low and/or substantially non-existent background signal from probe-ions in other locations. Combined with the absence of auto-fluorescence, the disclosed systems and methods facilitate the efficient, accurate and reliable identification and/or measurement of probe-ion concentrations in relevant marker sites, without the undesired effects associated with conventional diagnostic systems/techniques, e.g., conventional optical biopsy systems and techniques.

Additional advantageous features, functions and benefits associated with the disclosed systems and methods will be apparent from the description which follows, particularly when read in conjunction with the appended figures.

To assist those of ordinary skill in the art in making and using the disclosed systems and methods, reference is made to the appended figures, wherein.

Figure 4:
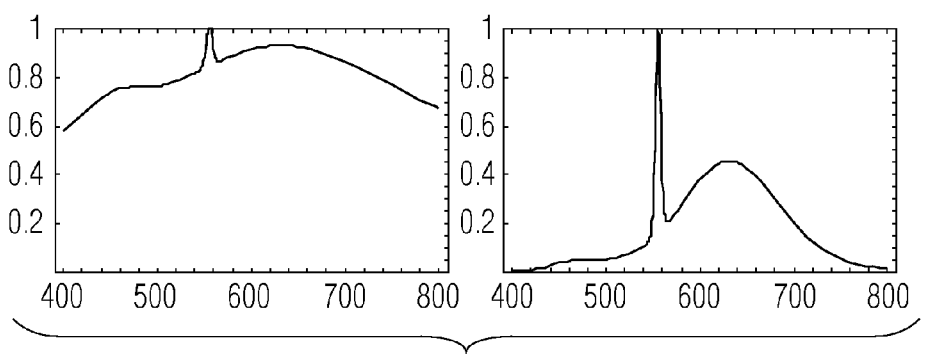
Figure 5:
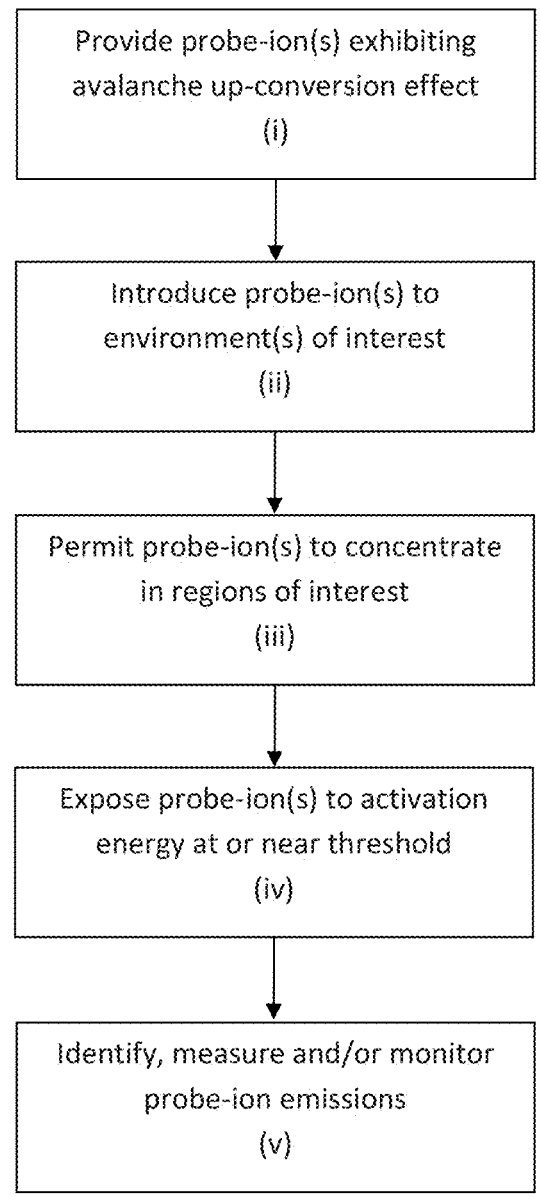

FIG. 4 includes a pair of plots showing normalized emission spectra: the plot at the left shows the normalized emission spectra calculated below the requisite threshold and the plot at the right shows the normalized emission spectra calculated close to the requisite threshold; and FIG. 5 is a flow chart setting forth steps associated with an exemplary implementation of the disclosed system/method.

Increased sensitivity and/or selectivity in performing diagnostic procedures, e.g., optical biopsy, is achieved according to the disclosed systems and methods wherein probe-ions exhibiting a highly non-linear response to optical activation, i.e., a photon avalanche effect, are employed. The probe-ions are introduced to an anatomical environment of interest, e.g., through injection, ingestion or the like, and activation energy is supplied to such environment. The disclosed systems and methods exhibit increased sensitivity and/or selectivity based on the introduction of activation energy that is effective to initiate the avalanche effect for the selected probe-ion. Through the avalanche effect, small differences in probe-ion density and/or excitation power translate to a substantial differential in up-conversion emission intensity.

Through the use of the disclosed probe-ions, the systems and methods of the present disclosure accurately distinguish locations where the probe-ion concentration is high, e.g., above a desired threshold, while at the same time substantially eliminating background signals from probe-ions distributed at lower concentration throughout the measurement volume. In addition, background auto-fluorescence of surrounding healthy tissue is generally eliminated. Exemplary probe-ions for use according to the disclosed systems and methods include mixed rare earth/transition metal phosphors.

Figure 1:
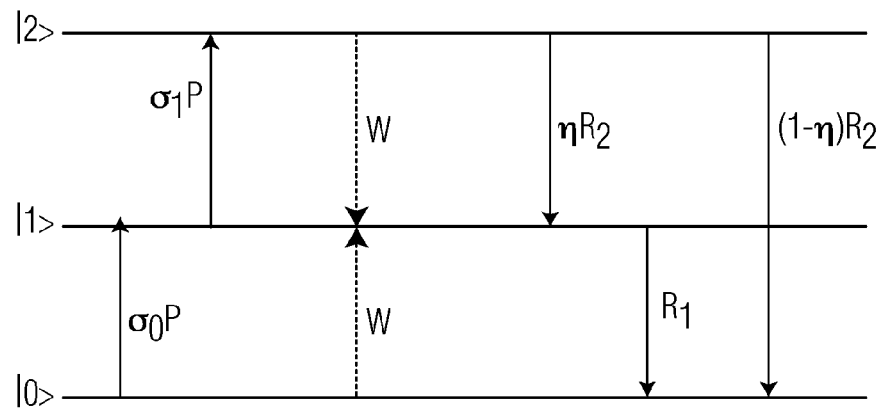
FIG. 1 is a schematic energy level diagram for an ion with three electronic states capable of avalanche up-conversion.

To further assist persons of ordinary skill in the art in understanding and employing the disclosed probe-ions, e.g., in connection with performing advantageous diagnostic procedures, additional information concerning up-conversion avalanche effects are provided herein. The up-conversion avalanche effect is relatively rare and, for probe-ions exhibiting and/or undergoing such effect, the avalanche effect occurs through an interplay between several competing absorption and energy transfer processes. With reference to FIG. 1, a schematic energy level diagram for an ion with three electronic states capable of avalanche up-conversion is provided. The upward arrows in FIG. 1 indicate absorption transitions, the downward arrows indicate emission transitions, and the set of dotted arrows indicates the cross-relaxation process.

Three special conditions are required to observe the up-conversion avalanche effect. First, the excitation radiation must not be resonant with the absorption transition from the ground state to the intermediate excited state $|0\rangle \rightarrow |1\rangle$. Second, the excitation radiation must be resonant with the absorption transition from the intermediate excited state to the upper excited state $|1\rangle \rightarrow |2\rangle$. Third, there must be a relatively strong cross-relaxation process $|0,2\rangle \rightarrow |1,1\rangle$ that can compete with radiative relaxation from the upper excited state $|2\rangle \rightarrow |0\rangle$.

For derivation purposes, P is used to denote the laser power; $N_i$ is the population density of state $|i\rangle$; $\sigma_0$ denotes the absorption cross-section for the ground state absorption ($|0\rangle \rightarrow |1\rangle$); and $\sigma_1$ denotes the absorption cross-section for the excited state absorption ($|1\rangle \rightarrow |2\rangle$). The radiative rate for the transition $|2\rangle \rightarrow |1\rangle$ is written as $\eta R_2$, while the radiative rate for the transition $|2\rangle \rightarrow |0\rangle$ is written as $(1-\eta)R_2$, where $\eta$ is the branching ratio. The radiative rate for the transition $|1\rangle \rightarrow |0\rangle$ is written as $R_0$. Finally, the cross-relaxation rate constant is denoted by W. Of note, the relaxation rate constant (W) is strongly dependent on the concentration of probe-ions, as cross-relaxation is a two-ion pair-process. Based on the foregoing definitions, the system of rate equations describing the populations of all three energy states are: $N_0$ $$\frac{\partial N_0}{\partial t} = -\sigma_0 P N_0 - W N_0 N_2 + R_1 N_1 + (1-\eta) R_2 N_2, \quad (1)$$

$$\frac{\partial N_1}{\partial t} = \sigma_0 P N_0 - \sigma_1 P N_1 + 2 W N_0 N_2 - R_1 N_1 + \eta R_2 N_2, \quad (2)$$

$$\frac{\partial N_2}{\partial t} = \sigma_1 P N_1 - W N_0 N_2 - R_2 N_2. \quad (3)$$

Of note, the factor "2" in Equation (2) is a direct result of the two-ion cross-relaxation process $|0,2\rangle \rightarrow |1,1\rangle$. Under steady state conditions $$\left(\frac{\partial N_2}{\partial t} = \frac{\partial N_1}{\partial t} = \frac{\partial N_0}{\partial t} = 0\right)$$

the solutions for this system of rate equations is:

$$N_2 = \frac{\sigma_1 P}{W N_0 + R_2} N_1 \approx \frac{\sigma_1 P}{W + R_2} N_1, \quad (4)$$

and $$N_1 = \frac{\sigma_0 P N_0}{R_1} + \frac{W N_0 - (1-\eta) R_2}{R_1} N_2 \approx \frac{\sigma_0 P}{R_1} + \frac{W - (1-\eta) R_2}{R_1} N_2, \quad (5)$$

when using $N_0 \approx 1$ for the approximations (i.e., no ground state bleaching is taken into consideration). By incorporating Equation (5) into Equation (4), the following result is obtained:

$$N_2 = \frac{\sigma_0 \sigma_1 P^2}{R_1(W + R_2) - \sigma_1 P(W - (1-\eta)R_2)}. \quad (6)$$

Of note, a critical power $P_C$ is implied:

$$P_C = \frac{R_1(R_2 + W)}{\sigma_1(W - (1-\eta)R_2)}, \quad (7)$$

for which Equation (6) diverges. The divergence of Equation (6) and the subsequent avalanche effect is graphically depicted in FIG. 2 (calculated for $\sigma_0=1$, $\sigma_1=5$, $R_1=1$, $R_2=10$, $W=100$, $\eta=0.5$).

Figure 2:
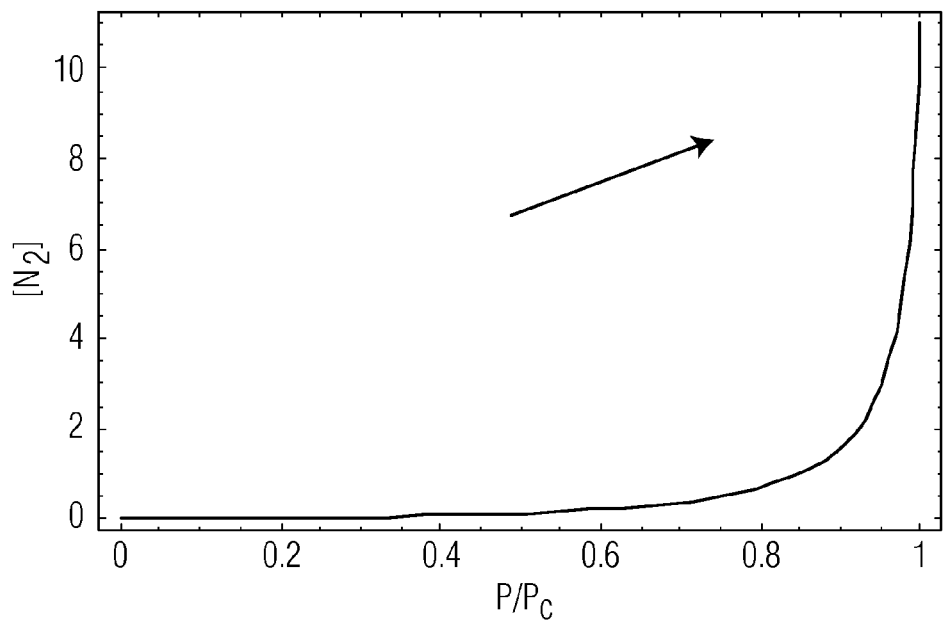
FIG. 2 is a graphical depiction of the divergence of power relative to the avalanche effect for an exemplary probe-ion exhibiting the avalanche effect.

More particularly, FIG. 2 depicts the population of state $|2\rangle$ as a function of normalized excitation power for an exemplary probe-ion. The avalanche effect can be seen for powers $P \approx P_C$, in accordance with Equations (6) and (7). As can be seen from Equation (6), a divergence of the up-conversion emission will occur easiest most readily/easily when W is large compared to $R_2$. There are a variety of probe-ions capable of up-conversion according to the present disclosure that satisfy the foregoing criterion.

For example, probe-ions exhibiting the desired up-conversion properties as described herein include the rare earth ions (where the radiative relaxation rates from the upper excited states is typically in the range of $10^4$-$10^6$ s$^{-1}$ and the cross-relaxation rate may be as large as $10^7$ s$^{-1}$). Rare earth ions in their trivalent state are particularly preferred according to the disclosed systems and methods.

In a further exemplary embodiment of the present disclosure, probe-ion systems that include mixed rare earth/transition metal phosphors may be employed in diagnostic procedures, e.g. optical biopsy. According to such exemplary embodiments, excitation energy is absorbed by the rare earth ion(s) included in the disclosed mixture, and such activation energy is subsequently transferred to the transition metal ion(s). Exemplary rare earth metals for use in the disclosed probe-ions include that $Yb^{3+}$ and $Tm^{2+}$, at least in part because such metals have only one (1) excited state (at roughly 10,000 cm$^{-1}$), which contains the full f-f oscillator strength and results in a significant absorption cross section.

In selecting transition metal ions for inclusion in the disclosed probe-ions, preferred transition metals do not exhibit absorption bands in the near-infrared range where the rare earth ion absorbs the initial excitation photon. However, preferred transition metals advantageously exhibit strong absorption bands at roughly twice the excitation energy, preferably over a broad energy range. Transition metals that exhibit such properties permit the selection/utilization of excitation energy levels that maximize the avalanche effect, i.e., such transition metals facilitate "tuning" of the disclosed systems and methods for enhanced performance.

Generally, the lowest excitation state should be above ~13'000 cm$^{-1}$ for purposes of the disclosed probe-ions. In instances where the foregoing excitation parameter threshold is applicable, transition metal ions having the following electronic configurations are generally employed: $3d^2$, $3d^3$, $3d^5$ and $3d^8$ (e.g., based on Tanabe-Sugano diagrams). Transition metal ions that exhibit the desired electronic configurations include, but are not limited to, $Cr^{3+}$, $Mn^{4+}$, $V^{2+}$, $Mn^{2+}$, $Ni^{4+}$, $Fe^{2+}$, $V^{3+}$, $Cr^{4+}$, $Cu^{2+}$ and $Ni^{2+}$. In addition, ions exhibiting $3d^4$ and $3d^6$ electronic configurations may be effectively incorporated into probe-ions according to the present disclosure, but such metal ions can be expected to be effective only in a very narrow crystal field range where the metal ion's first excited states are at sufficient energy. Depending on the exact site symmetry and crystal field strengths, the emitted color of the transition metal ions according to the present disclosure can be almost any wavelength spanning the green, yellow, orange and red spectral range.

In order to maximize the efficiency of the avalanche up-conversion process, the rare earth and transition metal ions are generally selected so as to be at a well-defined distance. According to preferred embodiments of the present disclosure, the rare earth and transition metal ions are at a well-defined distance, such distance being as close together as possible. In addition, the bridging angle between the two ions—i.e., the rare earth ion and the transition metal ion—is preferably corner sharing. A corner sharing configuration advantageously maximizes the wave function overlaps, which translates and/or yields super-exchange interaction between the two ions.

Figure 3:
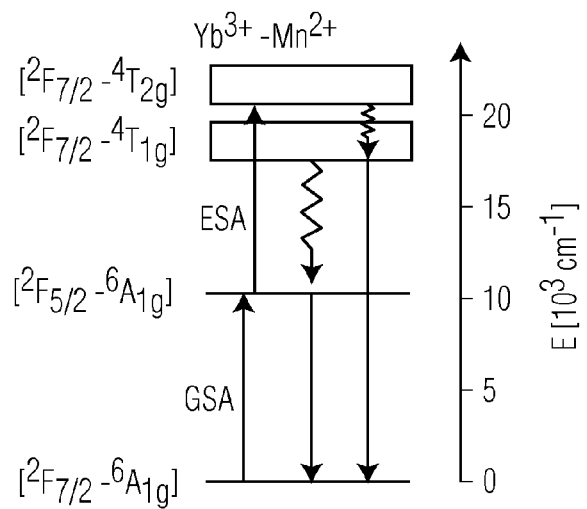
FIG. 3 is a graphical depiction of energy-related properties of a $Yb^{3+}$ and $Mn^{2+}$ ion couple according to the present disclosure.

According to an exemplary embodiment of the present disclosure, a probe-ion system is provided that includes a $Yb^{3+}$ and $Mn^{2+}$ ion couple. The energy-related behaviour/response of the foregoing ion couple is depicted in FIG. 3 (which is taken from Pascal Gerner et al., "Chem. Eur. J.," 10, 4735-4741, 2004). After non-resonant ground state absorption (GSA), the $Yb^{3+}$—$Mn^{2+}$ dimer is excited, but only slightly, into the $Yb^{3+}$ dominated $^2F_{5/2}$ excited state. After absorption of a second excitation photon, the $Yb^{3+}$—$Mn^{2+}$ dimer is further excited into the $Mn^{2+}$ dominated $^4T_1/^4T_2$ bands. The precise excitation state depends on the excitation energy received by the dimer. Subsequent rapid thermalization leaves $Mn^{2+}$ in its red/green emitting $^4T_1$ excited state. The precise color of the emission light is tunable via the crystal field strength, allowing a degree of freedom in design of the ideal phosphor. Typical avalanche up-conversion emission should then be observable, e.g., in bromides (e.g. $MnBr_2$:$Yb^{3+}$), chlorides ($MnCl_2$:$Yb^{3+}$) and other halides (such as $RbMnCl_3$:$Yb^{3+}$, $CsMnCl_3$:$Yb^{3+}$, $CsMnBr_3$:$Yb^{3+}$, $RbMnBr_3$:$Yb^{3+}$, $Rb_2MnCl_4$:$Yb^{3+}$).

The disclosed systems and methods utilize the avalanche effect to clearly distinguish probe-ions at a desired location from background probe-ion concentrations separately located relative to the desired location. Depending on how close the activation energy is to the requisite threshold, the magnitude of the emission associated with the up-conversion will be influenced/effected. A small variation in the concentration of the avalanche up-conversion ions translates/results in a large change in the cross-relaxation rate constant W. This, in turn, will significantly change the population in the upper excited state (assuming the excitation power is maintained constant).

A typical example of the avalanche up-conversion effect associated with the present disclosure is graphically depicted in FIG. 4. Normalized emission spectra are calculated to be below the requisite threshold in the left plot, and the normalized emission spectra are calculated to be close to the threshold in the right plot. Of note, the desired probe-ion emission at 550 nm is more pronounced in the right spectrum as compared to the left spectrum. The only difference between these spectra is the influence of cross-relaxation (which in turn determines the ratio $P/P_C$). In the left graph, a desired luminescence at 550 nm on a strong background is observed, as would be the case in a normal/conventional optical biopsy procedure. In stark contrast, in the graph on the right of FIG. 4, the desired luminescence at 550 nm is shown when an exemplary avalanche up-conversion phosphor according to the present disclosure is exposed to excitation power, wherein the highest-intensity signal is close to threshold. Clearly, the 550 nm emission is much more pronounced with the avalanche up-conversion phenomena of the present disclosure, and the background signal is much weaker. Therefore, the 550 nm emission is much better resolved through implementation of the disclosed systems and methods, as depicted in the right graph of FIG. 4.

With reference to FIG. 5, an exemplary flow chart for implementation of the disclosed system and method is provided. As shown therein, an exemplary method/technique for identifying, measuring and/or monitoring probe-ion emissions so as to identify higher concentration regions involves: (i) providing probe-ion(s) that exhibit the avalanche up-conversion effect, (ii) introducing the probe-ions to anatomical and/or clinical environments of interest, (iii) permitting the probe-ions to concentrate in region(s) of interest, (iv) exposing the probe-ions to activation energy that is at or near the applicable threshold to initiate an avalanche up-conversion, and (v) identifying, measuring and/or monitoring probe-ion emissions so as to identify higher concentration region(s). The disclosed method (and systems supporting such method) have wide ranging applicability, e.g., in gene diagnosis, immunodiagnosis, medicinal development, environmental testing, biotechnology, fluorescent inspection, and the like. A particularly advantageous application of the disclosed method and associated system involves diagnostic procedures, e.g., optical biopsy.

Although the systems and methods of the present disclosure have been described with reference to exemplary embodiments thereof, the present disclosure is not limited by or to such exemplary embodiments. Rather, the disclosed exemplary embodiments are merely illustrative of applications, implementations and advantages associated with the disclosed systems and methods. Indeed, the present disclosure is intended to encompass modifications, enhancements and variations of the disclosed systems and methods, as would be readily apparent to persons of skill in the art based on the present disclosure, and which embody the spirit and/or scope of the present disclosure.

The invention claimed is:

1. A method for identifying a region or location of interest, comprising:
    providing one or more probe-ions adapted to exhibit an avalanche up-conversion effect to a region or location of interest;
    exposing the probe-ions to an activation energy which initiates an avalanche up-conversion effect of selected probe-ions located in one or more regions where concentration of the probe-ions exceeds a concentration threshold; and
    identifying the one or more regions where the concentration of the probe-ions exceeds the concentration threshold based on emissions associated, at least in part, with the avalanche up-conversion effect of the selected probe-ions,
    wherein the avalanche up-conversion effect is not initiated in unselected probe-ions of the probe-ions outside the one or more regions where concentration of the probe-ions exceeds the concentration threshold.

2. The method according to claim 1, wherein the probe-ions are introduced to one of an anatomical environment or a clinical environment comprising the one or more regions.

3. The method according to claim 2, wherein the probe-ion(s) is/are functionalized so as to concentrate in a region and/or location of interest.

4. The method according to claim 1, wherein the activation energy is delivered at an energy level that is at or near a threshold for initiating an up-conversion avalanche effect for the probe-ions.

5. The method according to claim 1, further comprising: differentiating between the one or more regions of higher concentration of probe-ions and background levels of based on the emissions initiated by the activation energy.

6. The method according to claim 1, wherein the activation energy does not initiate auto-fluorescence of tissue at a level sufficient to interfere with a recited determination.

7. The method according to claim 1, wherein at least one of the probe-ions includes a combination of rare earth and transition metal ions.

8. The method according to claim 7, wherein the rare earth ion is $Yb^{3+}$.

9. The method according to claim 7, wherein at least one of the probe-ions is a mixed rare earth/transition metal phosphor.

10. The method according to claim 7, wherein the transition metal ion is selected from the group consisting of $Cr^{3+}$, $Mn^{4+}$, $V^{2+}$, $Mn^{2+}$, $Ni^{4+}$, $Fe^{2+}$, $V^{3+}$, $Cr^{4+}$, $Cu^{2+}$ and $Ni^{2+}$.

11. The method according to claim 7, wherein the transition metal ion is characterized by an electronic state of $3d^2$, $3d^3$, $3d^5$ or $3d^8$.

12. The method according to claim 7, wherein the rare earth and transition metal ions are selected so as to be at a well-defined distance.

13. The method according to claim 12, wherein a bridging angle between the rare earth ion and the transition metal ion involves corner sharing.

14. The method according to claim 1, wherein each of the probe-ions comprise a halide host lattice configured to incorporate both a rare earth ion and a transition metal ion.

15. The method according to claim 14, wherein the halide host lattice is effective for emissions that facilitate the recited determination.

16. The method according to claim 14, wherein the transition metal ion comprises one of $MnBr_2:Yb^{3+}$), $MnCl_2:Yb^{3+}$, $RbMnCl_3:Yb^{3+}$, $CsMnCl_3:Yb^{3+}$, $CsMnBr_3:Yb^{3+}$, $RbMnBr_3:Yb^{3+}$, or $Rb_2MnCl_4:Yb^{3+}$.

17. The method according to claim 1, wherein the determination is associated with an application comprising at least one of gene diagnosis, immunodiagnosis, medicinal development, environmental testing, biotechnology, fluorescent inspection, and optical biopsy.

18. The method according to claim 1, further comprising:
tuning an avalanche emission wavelength of the activation energy with a crystal field.

19. A method for identifying a region interest in an environment of interest, comprising:
introducing probe-ions into the environment of interest, the probe-ions being configured to exhibit avalanche up-conversion effect;
permitting the probe-ions to concentrate in at least one location having a probe-ion density exceeding a concentration threshold and in at least one other location having a probe-ion density less than the concentration threshold;
exposing the probe-ions to activation energy at or near a threshold energy for initiating the avalanche up-conversion, the activation energy causing the probe-ions in the location having the probe-ion density exceeding the concentration threshold to exhibit the avalanche up-conversion effect; and
measuring probe-ion emissions of the probe-ions in the location having the probe-ion density exceeding the concentration threshold.

* * * * *